United States Patent [19]
Lim et al.

[11] Patent Number: 5,980,584
[45] Date of Patent: Nov. 9, 1999

[54] SUBSTITUTED P-AMINOPHENOL, PROCESS OF PREPARATION AND USE IN DYEING HAIR

[75] Inventors: Mu-III Lim, Trumbull; Linas R. Stasaitis, Fairfield; Yuh-Guo Pan, Stamford; Michael Y. M. Wong, Easton, all of Conn.

[73] Assignee: Bristol-Myers Squibb Company, New York, N.Y.

[21] Appl. No.: 09/185,023

[22] Filed: Nov. 3, 1998

[51] Int. Cl.⁶ .......................... A61K 7/13; C07C 215/76; C07C 209/36
[52] U.S. Cl. .................................. 8/408; 8/421; 564/418; 564/420; 564/423; 564/443
[58] Field of Search ..................................... 564/443, 418, 564/420, 423; 8/421, 408, 412, 649

[56] References Cited

U.S. PATENT DOCUMENTS

| | | | |
|---|---|---|---|
| 4,997,451 | 3/1991 | Clausen et al. | 8/421 |
| 5,047,066 | 9/1991 | Mano et al. | 8/421 |
| 5,344,463 | 9/1994 | Chan et al. | 8/412 |
| 5,364,413 | 11/1994 | Junino et al. | 8/421 |
| 5,703,266 | 12/1997 | Lagrange et al. | 564/443 |
| 5,752,983 | 5/1998 | Audousset et al. | 8/412 |
| 5,814,106 | 9/1998 | Audousset | 8/412 |

FOREIGN PATENT DOCUMENTS

| | | |
|---|---|---|
| 3543345 | 6/1987 | Germany . |
| 3441148 | 5/1998 | Germany . |
| 94/27564 | 12/1994 | WIPO . |
| 96/28405 | 9/1996 | WIPO . |

OTHER PUBLICATIONS

English language translation of EP 182, 187, Wella, pp. 1–18, May 1986.

*Primary Examiner*—Caroline D. Liott
*Attorney, Agent, or Firm*—Morton S. Simon; Charles J. Zeller; Thomas R. Savitsky

[57] ABSTRACT

The novel primary intermediate, 1-(5-amino-2-hydroxyphenyl)ethane-1,2-diol and a method for producing same, are disclosed. The novel intermediate can be employed as a replacement for p-aminophenol in oxidation dye formulations.

9 Claims, No Drawings

SUBSTITUTED P-AMINOPHENOL, PROCESS OF PREPARATION AND USE IN DYEING HAIR

FIELD OF THE INVENTION

The invention relates to a new substituted p-aminophenol, a process for preparing same and to its use in compositions for dyeing human hair.

BACKGROUND OF THE INVENTION

Compositions for oxidative hair coloring comprise primary intermediates such as p-phenylenediamine and p-aminophenol and couplers such as resorcinol, 3-aminophenol, 5-amino-2-methylphenol and 2,4-diaminophenoxyethanol. However, as noted in U.S. Pat. No. 4,997,451, the use of p-aminophenol (PAP) is being questioned for toxicological reasons.

Because of the toxicological issues, the art has been looking for substitutes for p-aminophenol.

U.S. Pat. No. 4,997,451 describes oxidative hair dyeing compositions based on new 4-aminophenol primary intermediates of the formula 2 which provide oxidative hair dyeing compositions useful for producing red shades. These red shades are comparable in color intensity and brightness to those produced utilizing 4-aminophenol. Moreover, dyes produced through use of the primary intermediates of formula 2 possess a superior toxicological profile.

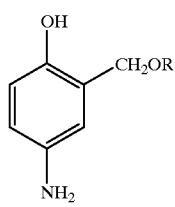

2. R = mono, dihydroxyalkyl($C_1$–$C_4$)
aminoalkyl($C_2$–$C_4$)

U.S. Pat. No. 5,047,066 teaches dye compositions for keratinous fibers. The dye compositions contain a 2-substituted 4-aminophenol compound of the general formula 3, 4, 5, and 6, as a developer, and a coupling substance.

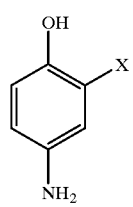

X = NHCOR
X = COOR

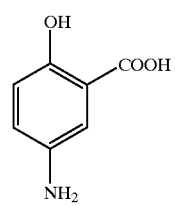

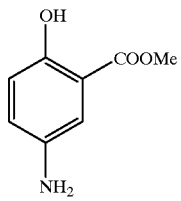

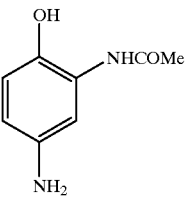

Compounds 4 and 5 couple with 1-naphthol to produce a vivid reddish hair color. Patentees claim that the new primary intermediates overcome problems of insufficient performance in terms of saturation or vividness of colors, dyeing capability and fastness.

DE 3,441,148 discloses hair dyes containing 4-aminohydroxyalkylphenols of the formula 7 as developers.

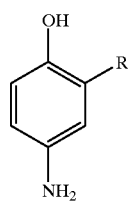

R = $C_1$–$C_4$ Monohydroxyalkyl

U.S. Pat. No. 5,364,413 teaches 3-substituted p-aminophenols of the formula 8, a process for preparing these compounds, their use for dyeing keratinous fibers and the intermediate compounds used in the preparation process.

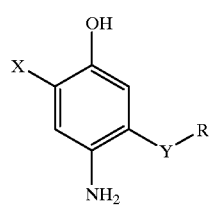

X = H, Halogen
Y = O, S
R = alkyl, hydroxyalkyl

WO 94/27564 teaches the use of 3-substituted p-aminophenols of the formula 9 for dyeing keratinous fibers and novel 3-substituted p-aminophenols.

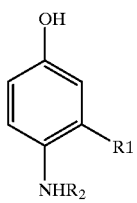

R₁ = Alkyl, alkenyl, mono or polyhydroxyalkyl
R₂ = H, alkyl, mono or dihydroxyalkyl
R₁ is not Me, CF₃.

DE 3,543,345 discloses oxidative hair dyes based on 4-amino-2-aminomethylphenol of the formula 10.

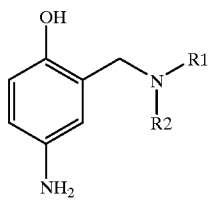

Although many p-aminophenol derivatives have been patented, only two of them, i.e., 3-methyl-4-aminophenol and 2-aminomethyl-4-aminophenol, are used in commercial hair coloring products. They are primary intermediates. Upon oxidation they couple with conventional couplers to produce an oxidative hair dye. However, these compounds cannot be used as a direct replacement for 4-aminophenol mainly due to color differences. For example, 2-aminomethyl-4-aminophenol couples with 2-methyl-5-aminophenol to color piedmont hair red brown, while a combination of 4-aminophenol and 2-methyl-5-aminophenol colors hair bright orange-red. 3-Methyl-4-aminophenol generally causes a bathochromic shift, as compared to 4-aminophenol.

The object of the invention is to develop a direct replacement for p-aminophenol which, when employed with conventional couplers in oxidative dyeing, gives colors close to that obtained when p-aminophenol is employed with such couplers. This is important because direct replacement allows one skilled in the art to formulate shades based on the existing shades, thereby reducing development time.

BRIEF SUMMARY OF THE INVENTION

The present invention relates to the novel compound 1-(5-amino-2-hydroxyphenyl)ethane-1,2-diol, formula 1, a process for preparing same, its use as a primary intermediate in oxidative hair dyeing and hair dye compositions containing same.

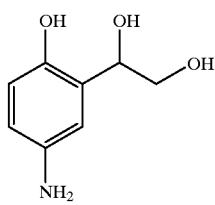

The present invention enables the skilled artisan to directly replace p-aminophenol in an existing oxidative dye formulation with the above compound 1 and obtain a dyeout close to that afforded by use of the p-aminophenol containing existing formulation.

Advantageously, the shades obtained through the use of the present novel compound have good wash and light fastness.

The process for the preparation of the present novel compound is new and commercially feasible. The synthesis of the compound 1 requires three steps: (1) simultaneous ring-opening and amino group substitution of 5-nitroisatin with an alkali metal hydroxide such as sodium hydroxide, potassium hydroxide or lithium hydroxide, (2) borane reduction of the keto acid, and (3) hydrogenation.

The present invention is also directed to an oxidative hair dye system comprising a primary intermediate and a coupler in a cosmetically acceptable vehicle wherein the intermediate and coupler are reacted in the presence of an oxidizing agent, to produce at least one oxidative hair dye, wherein the improvement comprises the primary intermediate is 1-(5-amino-2-hydroxyphenyl)ethane-1,2-diol.

The present invention is further directed to an oxidative hair dye system comprising a primary intermediate or a mixture of primary intermediates; a coupler, or a mixture of couplers; an oxidizing agent; and a cosmetically acceptable vehicle, the primary intermediate or mixture of primary intermediates, the coupler or mixture of couplers, and the oxidizing agent being present in respective amounts such that a tinctorially effective amount of at least one oxidative hair dye is produced in said vehicle, wherein the improvement comprises 1-(5-amino-2-hydroxyphenyl) ethane-1,2-diol is employed as a primary intermediate in said system.

DETAILED DESCRIPTION OF THE INVENTION

The following examples are intended to illustrate the present invention and not to limit same in any respect. It should be noted that where percentage is employed, unless indicated to the contrary, it is percent by weight and is based on total weight.

The invention relates to the process for preparing the compounds of the formula 1. The process is very unique. This uniqueness is demonstrated by comparison with the synthesis of structurally similar 2-(hydroxyalkyl)-4-aminophenol. For example, the synthesis of 2-(hydroxyalkyl)-4-aminophenol described in DE 3,441,148 begins with commercially available 2-hydroxyalkylaniline (1) protection of hydroxyl and amino groups, (2) nitration, (3) deprotection, (4) transformation of amino to hydroxyl group and (5) final reduction to produce the target compounds. The process of the present invention uses commercially available 5-nitroisatin. The present process involves: (1) opening the lactam, (2) reduction with borane and (3) catalytic hydrogenation to afford compound 1. The present process is much simpler and less expensive than the prior art process of DE 3,441,148.

The synthesis of compound 1 was carried out according to the following scheme.

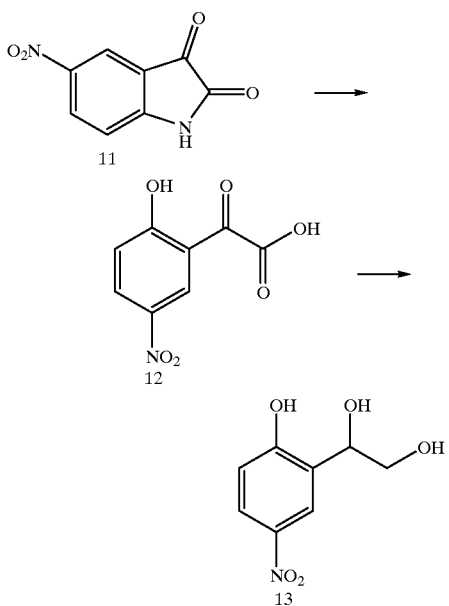

EXAMPLE 1

Treatment of 5-nitroisatin 11 (96.07 g, 500 mmole) with sodium hydroxide solution (750 mL, 1.5 M solution) in water (650 mL) at 95° C. for 24 hours affords compound 12 (137.50 g, 100% yield) after acidification to pH 2–3 with concentrated hydrochloric acid: mp 259.1–260.4° C. The α-ketoacid 12 (137.50 g, 500 mmol) is subjected to reduction with 1.0 M borane-THF complex in THF (1.5 L). The borane-THF complex is added dropwise to a suspension of 12 in THF (500 mL) at 4° C. over a period of 2.5 hours under nitrogen atmosphere. After the addition is complete, the reaction mixture is warmed to ambient temperature and stirred for a total of 24 hours. The excess borane is quenched at 4° C. with methanol and the solvents evaporated under vacuum. The residue is dissolved in 500 mL water and acidified to pH 2–3 with concentrated hydrochloric acid to afford compound 13 (93.94 g, 94.4% yield): mp 228–230.5° C. MS m/z=199. Parr hydrogenation of 13 (23.88 g, 120 mmole) with 10% Pd/C (2.4 g) in $CH_3OH$ (150 mL) for 2 hours affords compound 1 (20.32 g, 100%): mp 121–123° C.: $^1$HNMR (400 MHz, DMSO-$d_6$) δ 3.19 (m, 1H), 3,43 (m, 1H), 4.38 (bs, 2H), 4.63 (t, 1H, J=5.8 Hz), 4.73 (m, 1H), 4.98 (d, 1H, J=4.0 Hz), 6.27 (dd, 1H, J=8.0, 2.7 Hz), 6.41 (d, 1H, J=8.0 Hz), 6.57 (d, 1H, J=2.7 Hz), 8.30 (s, 1H); MS m/z=169.

Compositions

Dye compositions containing 1-(5-amino-2-hydroxyphenyl)ethane-1,2-diol can also contain one or more other primary intermediates and couplers.

These primary intermediates and couplers are selected from the following.

Suitable primary intermediates include:

p-Phenylenediamine derivatives such as: p-toluenediamine; p-phenylenediamine; 2-chloro-p-phenylenediamine; N-phenyl-p-phenylenediamine; N-2-methoxyethyl-p-phenylenediamine; N,N-bis(2-hydroxyethyl)-p-phenylenediamine, 2-hydroxymethyl-p-phenylenediamine; 2-hydroxyethyl-p-phenylenediamine; 4,4'-diaminodiphenylamine; 2,6-dimethyl-p-phenylenediamine; 2-iso-propyl-p-phenylenediamine; N-(2-hydroxypropyl)-p-phenylenediamine; 2-propyl-p-phenylenediamine; 1,3-bis(N-hydroxyethyl)-N-(4-aminophenyl)amino-2-propanol and 2-methyl-4-dimethylaminoaniline; 1-(2, 5-diaminophenyl)ethylene glycol;

p-Aminophenol derivatives such as: p-aminophenol; p-methylaminophenol; 3-methyl-p-aminophenol; 2-hydroxymethyl-p-aminophenol; 2-methyl-p-aminophenol; 2-(2'-hydroxyethylaminomethyl)-p-aminophenol; 2-methoxymethyl-p-aminophenol and 5-aminosalicylic acid;

Ortho-developers such as: catechol; pyrogallol; o-aminophenol; 2,4-diaminophenol; 2,4,5-trihydroxytoluene; 1,2,4-trihydroxybenzene; 2,3-dihydroxynaphthalene; 5-methyl-o-aminophenol; 6-methyl-o-aminophenol and 2-amino-5-acetaminophenol and;

Heterocyclic derivatives such as: 2,4,5,6-tetra-aminopyrimidine; 4,5-diamino-1-methyl-pyrazole and 2-dimethylamino-5-aminopyridine;

Suitable couplers include:

Phenols, resorcinol and naphthol derivatives such as: 1,7-dihydroxynaphthalene; resorcinol; 4-chlororesorcinol; 1-naphthol; 2-methyl-1-naphthol; 1-acetoxy-2-methylnaphthalene; 1,5-dihydroxynaphthalene; 2,7-dihydroxynaphthalene; hydroquinone; 2-methylresorcinol; 1-hydroxy-6-aminonaphthalene-3-sulfonic acid; thymol (2-isopropyl-5-methylphenol); 1,5-dihydroxy-1,2,3, 4-tetrahydronaphthalene; 2-chlororesorcinol; 2,3-dihydroxy-1,4-naphthoquinone and 1-naphthol-4-sulfonic acid;

m-Phenylenediamines such as: m-phenylenediamine; 2,4-diaminophenoxyethanol; N,N-bis(hydroxyethyl)-m-phenylenediamine; 2,6-diaminotoluene; 2-N,N-bis(hydroxyethyl)-2,4-diaminophenetole; bis(2,4-diaminophenoxy)-1,3-propane; 1-hydroxyethyl-2,4-diaminobenzene; 2-amino-4-hydroxyethylaminoanisole; 1-aminoethoxy-2,4-diaminobenzene; 2,4-diaminophenoxyacetic acid; 4,6-bis(hydroxyethoxy)-m-phenylenediamine; 2,4-diamino-5-methylphenetole; 2,4-diamino-5-hydroxyethoxytoluene; 2,4-dimethoxy-1,3-diaminobenzene and 2,6-bis(hydroxyethylamino)-toluene;

m-Aminophenols such as: m-aminophenol; 2-hydroxy-4-carbamoylmethylamino toluene; m-carbamoylmethylaminophenol; 6-hydroxybenzomorpholine; 2-hydroxy-4-aminotoluene; 2-hydroxy-4-hydroxyethylaminotoluene; 4,6-dichloro-m-aminophenol; 2-methyl-m-aminophenol; 2-chloro-6-methyl-m-aminophenol; 2-hydroxyethoxy-5-aminophenol; 2-chloro-5-trifluoroethylaminophenol; 4-chloro-6-methyl-m-aminophenol; N-cyclopentyl-3-aminophenol; N-hydroxyethyl-4-methoxy-2-methyl-m-aminophenol and 5-amino-4-methoxy-2-methylphenol and Heterocyclic derivatives such as: 1-phenyl-3-methyl-5-pyrazolone; 6-ethoxy-8-aminoquinoline; 2,6-dihydroxy-4-methylpyridine; 5-hydroxy-1,4-enzodioxane; 3,4-methylenedioxyphenol; 4-hydroxyethylamino-1,2-ethylenedioxybenzene; 2,6-dihydroxy-3,4-dimethylpyridine; 5-chloro-2,3-dihydroxypyridine; 3,5-diamino-2,6-dimethoxypyridine; 2-hydroxyethylamino-6- methoxy-3-aminopyridine; 3,4-methylenedioxyaniline; 2,6-bis(2-hydroxyethoxy)-3,5-diaminopyridine; 4-hydroxyindole; 3-amino-5-hydroxy-2,6-dimethoxypyridine; 5,6-dihydroxyindole; 7-hydroxyindole; 5-hydroxyindole; 2-bromo-4,5-5methylenedioxyphenol; 6-hydroxyindole; 3-amino-2-methylamino-6-methoxypyridine; 2-amino-3-hydroxypyridine; 2,6-diaminopyridine; 5-(3,5-diamino-2-pyridyloxy)-1,3-dihydroxypentane; 3-(3, 5-diamino-2-pyridyloxy)-2-hydroxypropanol and 4-hydroxy-2,5,6-triaminopyrimidine.

Combinations of any of the above are also contemplated.

Preferred primary intermediates include:

p-Phenylenediamine derivatives such as: p-toluenediamine; p-phenylenediamine; N-2-methoxyethyl-p-phenylenediamine; N,N-bis(2-hydroxyethyl)-p-phenylenediamine; 2-hydroxyethyl-p-phenylenediamine; 1-(2,5-diaminophenyl)ethane-1,2 diol p-Aminophenol derivatives such as: p-aminophenol; p-methylaminophenol; 3-methyl-p-aminophenol and 2-methoxymethyl-p-aminophenol;

Ortho-developers such as: o-aminophenol; 1,2,4-trihydroxybenzene; 2-ethylamino-p-cresol; 5-methyl-2-aminophenol; 6-methyl-2-aminophenol and 2-amino-5-acetaminophenol and Heterocyclic derivatives such as: 2,4,5,6-tetra-aminopyrimidine and 4,5-diamino-1-methylpyrazole.

Preferred couplers include:

Phenols, resorcinol and naphthol derivatives such as: 2-methyl-1-naphthol; 1-acetoxy-2-methylnaphthalene; 1,7-dihydroxynaphthalene; resorcinol; 4-chlororesorcinol; 1-naphthol; 1,5-dihydroxynaphthalene; 2,7-dihydroxynaphthalene; hydroquinone; 2-methylresorcinol and thymol (2-isopropyl-5-methylphenol);

m-Phenylenediamines such as: m-phenylenediamine; 2,4-diaminophenoxyethanol; 1,3-bis(2,4-diaminophenoxy) propane; 2-amino-4-hydroxyethylamino anisole and 1,3-bis(2,4-diaminophenoxy)propane; 4,6-bis(hydroxyethoxy)-m-phenylenediamine;

m-Aminophenols such as: m-aminophenol; 6-hydroxybenzomorpholine; 2-hydroxy-4-aminotoluene, 2-hydroxy-4-hydroxyethylaminotoluene and 2-methyl-m-aminophenol and Heterocyclic derivatives such as: 4,5-diamino-1-methyl-pyrazole; 2-dimethylamino-5-aminopyrimidine; 1-phenyl-3-methyl-5-pyrazolone; 3,4-methylenedioxyphenol; 3,4-methylenedioxyaniline; 4-hydroxyindole; 5,6-dihydroxyindole; 7-hydroxyindole; 5-hydroxyindole, 6-hydroxyindole; and 2,6-diaminopyridine.

Most preferred primary intermediates include:

p-Phenylenediamine derivatives such as: p-toluenediamine; p-phenylenediamine; N,N-bis(2-hydroxyethyl)-p-phenylenediamine and 2-hydroxyethyl-p-phenylenediamine; 1-(2,5-diaminophenyl)ethane-1,2-diol p-Aminophenol derivatives such as: p-aminophenol; p-methylaminophenol and 3-methyl-p-aminophenol;

Ortho-developers such as: o-aminophenol; 1,2,4-trihydroxybenzene; 2-ethylamino-p-cresol; 5-methyl-2-aminophenol; 6-methyl-2-aminophenol and 2-amino-5-acetaminophenol.

Most preferred couplers include:

Phenols, resorcinol and naphthol derivatives such as: 2-methyl-1-naphthol; 1-acetoxy-2-methylnaphthalene; resorcinol; 4-chlororesorcinol; 1-naphthol and 2-methylresorcinol;

m-Phenylenediamines such as: 2,4-diaminophenoxyethanol and 2-amino-4-hydroxyethylamino anisole; and Heterocyclic derivatives such as: 4,5-diamino-1-methyl-pyrazole: 1-phenyl- 3-methyl-5-pyrazolone and 6-hydroxyindole.

Mixtures are also contemplated.

Preferred combinations employing 1-(5-amino-2-hydroxyphenyl) ethane-1,2-diol as a p-aminophenol replacement include combinations 1-36 set forth in Table 1 which follows. The Combination 1 of Table 1 is a mixture of 1-(5-amino-2-hydroxyphenyl) ethane-1,2-diol, p-phenylene-diamine, o-aminophenol, resorcinol, 1-naphthol, and m-aminophenol.

In reading Table 1, reading down the column headed 2, the components of combination 2 are indicated by xes.

The composition of each of the remaining combinations is similarly determined.

TABLE 1

| Structure | IUPAC Name | Name | 1 | 2 | 3 | 4 | 5 | 6 | 7 | 8 | 9 | 10 | 11 | 12 | 13 | 14 | 15 | 16 | 17 | 18 |
|---|---|---|---|---|---|---|---|---|---|---|---|---|---|---|---|---|---|---|---|---|
| ![structure] HO-C6H3(OH)(NH2)-CH(OH)-CH2OH | 1-(5-Amino-2-hydroxyphenyl)-ethane-1,2-diol | 1-(5-amino-2-hydroxyphenyl)-ethane-1,2-diol | X | X | X | X | X | X | X | X | X | X | X | X | X | X | X | X | X | X |
| H2N-C6H4-NH2 | Benzene-1,4-diamine | p-phenylene-diamine | X | X | X | X | X | X | X | X | | | | | | | | | | |
| H2N-C6H3(NH2)-CH(OH)-CH2OH | 1-(2,5-Diamino-phenyl)-ethane-1,2-diol | 1-(2,5-diamino-phenyl)ethylene glycol | | | | | | | | | X | X | X | X | X | X | X | | | |
| H2N-C6H4-N(CH2CH2OH)2 | 2-[(4-Amino-phenyl)-(2-hydroxyethyl)-amino]-ethanol | N,N-bis(2-hydroxyethyl)-p-phenylenediamine | | | | | | | | | | | | | | | | X | X | X |

TABLE 1-continued

| Structure | Name | Alt. name | | | | | | | | | |
|---|---|---|---|---|---|---|---|---|---|---|---|
| phenol with OH and NH₂ | 2-Amino-phenol | o-aminophenol | X | X | | | | X | X | | | X |
| benzene-1,3-diol | Benzene-1,3-diol | resorcinol | X | | X | X | X | X | X | X | X | |
| 2-methyl-benzene-1,3-diol | 2-Methyl-benzene-1,3-diol | 2-methyl-resorcinol | | | X | X | X | X | X | X | X | X |
| naphthalen-1-ol | Naphthalen-1-ol | 1-naphthol | | | X | X | X | X | X | X | X | X |
| 2-methyl-naphthalen-1-ol | 2-Methyl-naphthalen-1-ol | 2-methyl-1-naphthol | X | | | X | X | X | X | X | X | X |

TABLE 1-continued

| Structure | IUPAC Name | Name | 19 | 20 | 21 | 22 | 23 | 24 | 25 | 26 | 27 | 28 | 29 | 30 | 31 | 32 | 33 | 34 | 35 | 36 |
|---|---|---|---|---|---|---|---|---|---|---|---|---|---|---|---|---|---|---|---|---|
| (structure) | 2-(2,4-Diaminophenoxy)-ethanol | 2,4-diaminophenoxyethanol | | | | | | | X | X | | | | | | | | | | |
| (structure) | 3-Amino-phenol | m-aminophenol | | X | | | X | | | | | X | | | X | | X | | | |
| (structure) | 5-Amino-2-methyl phenol | 5-amino-2-methylphenol | | | | X | | | | | | | | | | | | | | |
| (structure) | 1H-indole-5,6-diol | 5,6-dihydroxy-indole | | | | | | X | | | | | | X | X | | | | | |
| (structure) | 2-Amino-pyridin-3-ol | 2-amino-3-hydroxypyridine | | | | | | | | | X | X | | | | | | X | | |
| (structure) | 1-(5-Amino-2-hydroxy-phenyl)-ethane-1,2-diol | 1-(5-amino-2-hydroxyphenyl)-ethane-1,2-diol | X | X | X | X | X | X | X | X | X | X | X | X | X | X | X | X | X | X |

TABLE 1-continued

| | | | | | | | | | | | | | |
|---|---|---|---|---|---|---|---|---|---|---|---|---|---|
| Benzene-1,4-diamine | p-phenylene-diamine | | | | | | | | | | | | |
| 1-(2,5-Diamino-phenyl)-ethane-1,2-diol | 1-(2,5-diamino-phenyl)ethylene glycol | | | | x | x | x | x | x | | | | |
| 2-[(4-Amino-phenyl)-(2-hydroxyethyl)-amino]-ethanol | N,N-bis(2-hydroxyethyl)-p-phenylenediamine | x | x | x | x | x | x | x | x | x | | | |
| 2-Amino-phenol | o-aminophenol | | | | | | | | | x | x | x | x | x | x |

TABLE 1-continued

| Structure | Name | Alt. name | | | | | | | | | |
|---|---|---|---|---|---|---|---|---|---|---|---|
| (structure: benzene with two OH) | Benzene-1,3-diol | resorcinol | x | x | x | x | x | x | x | x | x |
| (structure: 2-methyl benzene-1,3-diol) | 2-Methyl-benzene-1,3-diol | 2-methyl-resorcinol | | x | x | x | x | x | x | x | x |
| (structure: naphthalen-1-ol) | Naphthalen-1-ol | 1-naphthol | x | x | x | x | x | x | x | | x |
| (structure: 2-methyl naphthalen-1-ol) | 2-Methyl-naphthalen-1-ol | 2-methyl-1-naphthol | x | x | | | | | | | x |
| (structure: 2-(2,4-diaminophenoxy)-ethanol) | 2-(2,4-Diamino-phenoxy)-ethanol | 2,4-diamino-phenoxyethanol | | | x x x x | x | x | | | | |

TABLE 1-continued

| | | 3-Amino-phenol | m-aminophenol | x | x | x | x | x | x | | | x | x |
|---|---|---|---|---|---|---|---|---|---|---|---|---|---|
| | | 5-Amino-2-methyl phenol | 5-amino-2-methylphenol | | | x | x | x | x | | | | |
| | | 1H-indole-5,6-diol | 5,6-dihydroxy-indole | | | | x | x | | x | x | x | |
| | | 2-Amino-pyridin-3-ol | 2-amino-3-hydroxypyridine | | | | | x | x | | | | |

The following composition shown in Table 2 is used for dyeing piedmont hair. The dyeing solution is mixed with 100 g of 20 volume hydrogen peroxide. The resulting mixture is applied to the hair and permitted to remain in contact with hair for 30 minutes. Thus dyed hair is then shampooed and rinsed with water and dried. The results are shown in Table 3, 4 and 5.

TABLE 2

Composition for the dyeing solution

| Ingredients | Weight % |
|---|---|
| Cocamidopropyl betaine | 17.00 |
| Monoethanolamine | 2.00 |
| Oleic acid | 0.75 |
| Citric acid | 0.10 |
| Ammonium hydroxide | 5.00 |
| Behentrimonium chloride | 0.50 |
| Sodium sulfite | 0.10 |
| EDTA | 0.10 |
| Erythorbic acid | 0.40 |
| Ethoxydiglycol | 3.50 |
| C11-15 Pareth-9 (Tergitol 15-S-9) | 1.00 |
| C12-15 Pareth-3(Neodol 25-3) | 0.50 |
| Isopropanol | 4.00 |
| Propylene glycol | 2.00 |
| Primary intermediate* | 5.00 mmole |
| Coupler* | 5.00 mmole |
| Water | qs to 100.00 |

*When compound 1 (DiOHPAP) is used, the weight of the primary intermediate and coupler is 0.75 mmole %.

The following Examples 2, 3, and 4 are illustrative examples of the general procedure employed when practicing the present invention.

EXAMPLE 2

1-(5-Amino-2-hydroxyphenyl)ethane-1,2-diol (compound 1, DiOHPAP) when coupled with 2-methyl-1-naphthol coupler produces a color which closely matches that obtained from the couple of 4-aminophenol with 2-methyl-1-naphthol. The color on piedmont hair is red, without violet tone, similar to the color derived from p-aminophenol (PAP) with 2-methyl-1-naphthol. The visual observation is also confirmed by CIBL*a*b* values (Table 3) obtained from coupling of 4-aminophenol, 1-(5-amino-2-hydroxyphenyl)ethane-1,2-diol, 2-methyl-4-aminophenol (2-MePAP) and 3-methyl-4-aminophenol (3-MePAP) with 2-methyl-1-naphthol. CIE b* value (which indicates direction of yellow and blue) decreases in order of 4-aminophenol, 1-(5-amino-2-hydroxyphenyl)ethane-1,2-diol, 2-methyl-4-aminophenol and 3-methyl-4-aminophenol. The b* value differences between PAP and compound 1, 2-methyl-4-aminophenol and 3-methyl-4-aminophenol, are 3.12, 6.26 and 10.92, respectively. Compound 1 shows the smallest differences among the various PAP derivatives tested. On the other hand, CIE a* values (which indicate red and green directions) undergo little change as compared to the large change in b* value. Hue angle difference ($\Delta h$) between PAP and compound 1 is 4.37. 2-MePAP and 3-MePAP show much larger hue angle difference, 11 and 18 respectively. This finding indicates that 1-(5-amino-2-hydroxyphenyl)ethane 1,2-diol 1 is a better alternative to 4-aminophenol than 2- or 3-methyl-4-aminophenol.

TABLE 3

Coupling of p-aminophenols with 2-methyl-1-naphthol

| | L* | a* | b* | C* | h |
|---|---|---|---|---|---|
| PAP | 41.24 | 29.90 | 16.64 | 34.22 | 29.09 |
| DiOHPAP 1 | 38.70 | 29.38 | 13.52 | 32.34 | 24.72 |
| 2-MePAP | 38.21 | 31.77 | 10.38 | 33.43 | 18.09 |
| 3-MePAP | 41.87 | 29.03 | 5.72 | 29.59 | 11.14 |

EXAMPLE 3

Another example also shows that 1-(5-amino-2-hydroxyphenyl)ethane-1,2-diol 1 when coupled with 2-methyl-5-(2-hydroxyethyl)aminophenol colors piedmont hair bright orange, a color very similar to the color obtained through use of 4-aminophenol and the same coupler. In the L*C*h color space, the Chroma C* value of dihydroxyethyl PAP 1 is the highest of the PAP derivatives tested (Table 4). This finding is surprising and unexpected. The chroma difference ($\Delta C^*$) between PAP and DiOHPAP is 1.3, while in the case of 2- and 3-MePAP, the differences are 3.56 and 6.09, respectively. C* (chroma) is defined as $C^* = \sqrt{(a^*)^2 + (b^*)^2}$. The value of chroma C* is 0 (gray color) at the center and increases according to the distance from the center. Increase of C* value indicates the color changes from gray to dull to vivid. Visual observation confirms our surprising finding that piedmont hair dyed with Compound 1 is more vivid than piedmont hair dyed with PAP (Table 4).

TABLE 4

Dyeing of p-aminophenol and its derivatives with 2-methyl-5-(2-hydroxyethylamino)phenol

| | L* | a* | b* | C* | h |
|---|---|---|---|---|---|
| PAP | 44.33 | 29.58 | 30.89 | 42.76 | 46.24 |
| DiOHPAP⁺ 1 | 45.57 | 31.75 | 30.55 | 44.06 | 43.89 |
| 2-MePAP | 44.06 | 28.64 | 26.77 | 39.20 | 43.06 |
| 3-MePAP | 54.01 | 26.86 | 24.96 | 36.67 | 42.90 |

EXAMPLE 4

1-(5-Amino-2-hydroxyphenyl)ethane-12-diol 1 couples with 2-methyl-5-aminophenol to color piedmont hair orange. In terms of C* and h values (Table 5), the color obtained is the closest to that derived from a dyeout with PAP and 2-methyl-5-aminophenol. Visual observation also leads to the same conclusion. The chroma difference ($\Delta C^*$) between PAP and DiOHPAP is 0.7, while in the case of 2- and 3-MePAP, the differences are 8.36 and 4.17, respectively.

TABLE 5

Dyeing of p-aminophenol and its derivatives with 2-methyl-5-aminophenol

| | L* | a* | b* | C* | h |
|---|---|---|---|---|---|
| PAP | 39.94 | 29.91 | 30.58 | 42.77 | 45.63 |
| DiOHPAP⁺ 1 | 45.54 | 30.69 | 30.79 | 43.47 | 45.10 |
| 2-MePAP | 39.00 | 24.91 | 23.73 | 34.41 | 43.61 |
| 3-MePAP | 50.69 | 28.98 | 25.50 | 38.60 | 41.35 |

EXAMPLE 5

The following compositions shown in Table 6 and Table 7 are mixed with 100 g of 20 volume hydrogen peroxide.

The resulting mixture is applied to gray hair and permitted to remain in contact with hair for 30 minutes. Thus dyed hair is then shampooed and rinsed with water and dried (Table 6 and 7).

TABLE 6

Composition for Dyeing Hair: Examples 1–5

| Ingredients | Example 1 WT % | Example 2 WT % | Example 3 WT % | Example 4 WT % | Example 5 WT % |
|---|---|---|---|---|---|
| Cocamidopropyl betaine | 17 | 17 | 17 | 17 | 17 |
| Ethanolamine | 2 | 2 | 2 | 2 | 2 |
| Oleic acid | 0.75 | 0.75 | 0.75 | 0.75 | 0.75 |
| Citric acid | 0.1 | 0.1 | 0.1 | 0.1 | 0.1 |
| Ammonium hydroxide | 5 | 5 | 5 | 5 | 5 |
| Behentrimonium chloride | 0.5 | 0.5 | 0.5 | 0.5 | 0.5 |
| Sodium sulfite | 0.1 | 0.1 | 0.1 | 0.1 | 0.1 |
| EDTA | 0.1 | 0.1 | 0.1 | 0.1 | 0.1 |
| Erythorbic acid | 0.4 | 0.4 | 0.4 | 0.4 | 0.4 |
| 1-(5-Amino-2-hydroxyphenyl)ethane-1,2-diol | 0.7 | 0.5 | 1 | 1.75 | 0.6 |
| N,N-Bis(2-hydroxyethyl)-p-phenylenediamine | 0.05 | | 0.3 | 0.02 | |
| p-Phenylenediamine | | | | 0.05 | |
| 1-(2,5-Diaminophenyl)ethylene glycol | 0.05 | | | | |
| Resorcinol | 0.5 | 0.1 | 0.1 | 1.2 | 0.1 |
| 4-Amino-2-hydroxytoluene | 0.3 | | | 1 | |
| 2-Methyl-5-hydroxyethylaminophenol | | 0.03 | 0.7 | | 0.05 |
| m-Aminophenol | 0.3 | | | 0.2 | |
| 1-Naphthol | 0.05 | 0.15 | | | 0.2 |
| 2-Methyl-1-naphthol | | | 1 | 0.15 | |
| 2,4-Diaminophenoxyethanol Hydrochloride | | | 0.01 | | |
| Water | qs to 100 | qs to 100 | qs to 100 | qs to 100 | qs to 100 |
| Color obtained on gray hair: | Auburn | Reddish blone | Burgundy | Red | Copper |

TABLE 7

Composition for Dyeing Hair: Examples 6–10

| Ingredients | Example 6 WT % | Example 7 WT % | Example 8 WT % | Example 9 WT % | Example 10 WT % |
|---|---|---|---|---|---|
| Cocamidopropyl betaine | 17 | 17 | 17 | 17 | 17 |
| Ethanolamine | 2 | 2 | 2 | 2 | 2 |
| Oleic acid | 0.75 | 0.75 | 0.75 | 0.75 | 0.75 |
| Citric acid | 0.1 | 0.1 | 0.1 | 0.1 | 0.1 |
| Ammonium hydroxide | 5 | 5 | 5 | 5 | 5 |
| Behentrimonium chloride | 0.5 | 0.5 | 0.5 | 0.5 | 0.5 |
| Sodium sulfite | 0.1 | 0.1 | 0.1 | 0.1 | 0.1 |
| EDTA | 0.1 | 0.1 | 0.1 | 0.1 | 0.1 |
| Erythorbic acid | 0.4 | 0.4 | 0.4 | 0.4 | 0.4 |
| 1-(5-Amino-2-hydroxyphenyl)ethane-1,2-diol | 0.25 | 0.35 | 0.2 | 0.03 | 1.5 |
| N,N-Bis(2-hydroxyethyl)-p-phenylenediamine | | | 0.08 | 0.4 | 3 |
| p-Phenylenediamine | 0.01 | | | 0.4 | |
| 1-(2,5-Diaminophenyl)ethylene glycol | | 0.55 | 0.4 | | |
| Resorcinol | 0.05 | 0.5 | 0.2 | 0.5 | 1 |
| 4-Amino-2-hydroxytoluene | | 0.1 | | | |
| 2-Methyl-5-hydroxyethylaminophenol | 0.06 | | | | |
| m-Aminophenol | 0.01 | 0.05 | 0.05 | 0.1 | 1 |
| 1-Naphthol | 0.01 | | 0.05 | | |
| 2-Methyl-1-naphthol | | 0.06 | | | 1 |
| 2,4-Diaminophenoxyethanol Hydrochloride | | | 0.01 | | 2 |
| Water | Qs to 100 | qs to 100 | qs to 100 | qs to 100 | qs to 100 |
| Color obtained on gray hair: | Golden blonde | Reddish brown | Light Brown | Dark brown | Black |

What is claimed is:

1. 1-(5-Amino-2-hydroxyphenyl)ethane-1,2-diol.

2. In an oxidative hair dye system comprising a primary intermediate and a coupler in a cosmetically acceptable vehicle wherein the intermediate and coupler are reacted in the presence of an oxidizing agent, to produce at least one oxidative hair dye, wherein the improvement comprises the primary intermediate is 1-(5-amino-2-hydroxyphenyl) ethane-1,2-diol.

3. The hair dye system of claim 2, further comprising at least one other primary intermediate.

4. The hair dye system of claim 2, further comprising at least one other coupler.

5. A method for producing 1-(5-amino-2-hydroxyphenyl) ethane-1,2-diol comprising:

reacting 5-nitroisatin with alkali metal hydroxide to produce a keto acid of the formula 12;

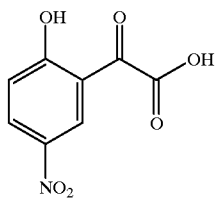

reducing the keto acid of formula 12 to produce a compound of formula 13;

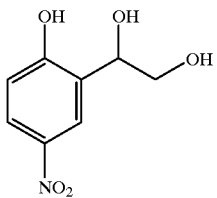

then hydrogenating the compound of formula 13 to convert the nitro group to an amino group, whereby said 1-(5-amino-2-hydroxyphenyl)ethane-1,2-diol is produced.

6. The method as claimed in claim 5, wherein the step of hydrogenating of compound 13 is carried out in the presence of 10% Pd/C.

7. The method as claimed in claim 5, wherein the keto acid of formula 12 is reduced with borane-tetrahydrofuran complex.

8. The method as claimed in claim 5, wherein the alkali metal hydroxide is sodium hydroxide, potassium hydroxide or lithium hydroxide.

9. In an oxidative hair dye system comprising a primary intermediate or a mixture of primary intermediates; a coupler, or a mixture of couplers; an oxidizing agent; and a cosmetically acceptable vehicle, the primary intermediate or mixture of primary intermediates, the coupler or mixture of couplers, and the oxidizing agent being present in respective amounts such that a tinctorially effective amount of at least one oxidative hair dye is produced in said vehicle, wherein the improvement comprises 1-(5-amino-2-hydroxyphenyl)ethane-1,2-diol is employed as a primary intermediate in said system.

* * * * *